United States Patent
Badger

[11] Patent Number: 5,885,257
[45] Date of Patent: Mar. 23, 1999

[54] SPRING LOADED AUTOMATIC RETRACTABLE NEEDLE SYRINGE

[76] Inventor: Peter Badger, 542 Frankston Dandenong Road, Carrum Downs Victoria, Australia

[21] Appl. No.: 820,709

[22] Filed: Mar. 18, 1997

[51] Int. Cl.[6] .................................................. A61M 5/00
[52] U.S. Cl. ............................................. 604/195; 604/110
[58] Field of Search .................................. 604/195, 263, 604/192, 198, 110, 220, 218

[56] References Cited

U.S. PATENT DOCUMENTS

| | | | |
|---|---|---|---|
| 2,696,212 | 12/1954 | Dunmire | 604/195 |
| 4,747,831 | 5/1988 | Kulli | 604/110 |
| 4,900,307 | 2/1990 | Kulli | 604/110 |
| 4,973,316 | 11/1990 | Dysarz | 604/195 |
| 5,026,354 | 6/1991 | Kocses | 604/220 X |
| 5,046,508 | 9/1991 | Weissler | 128/763 |
| 5,053,010 | 10/1991 | McGary et al. | 604/110 |
| 5,112,316 | 5/1992 | Venturini | 604/195 |
| 5,180,370 | 1/1993 | Gillespie | 604/195 X |
| 5,188,599 | 2/1993 | Botich et al. | 604/110 |
| 5,195,985 | 3/1993 | Hall | 604/195 |
| 5,201,719 | 4/1993 | Collins et al. | 604/195 |
| 5,484,414 | 1/1996 | Pace | 604/195 X |

FOREIGN PATENT DOCUMENTS

WO 92/18187  10/1992  WIPO .

*Primary Examiner*—John D. Yasko
*Attorney, Agent, or Firm*—Richard L. Moseley

[57] ABSTRACT

A spring loaded automatic retractable needle syringe is disclosed wherein a compressed spring is placed between a needle carrier and the distal end of the barrel and a cap placed over the distal end of the barrel. A releasable retaining means is provided to hold the needle carrier at the distal end. The needle extends through an opening in the end of the cap which is covered by a puncture pad. When the releasable retaining means is released the compressed spring pushes the needle carrier back up completely into the barrel. The puncture pad seals the opening in the cap.

9 Claims, 2 Drawing Sheets

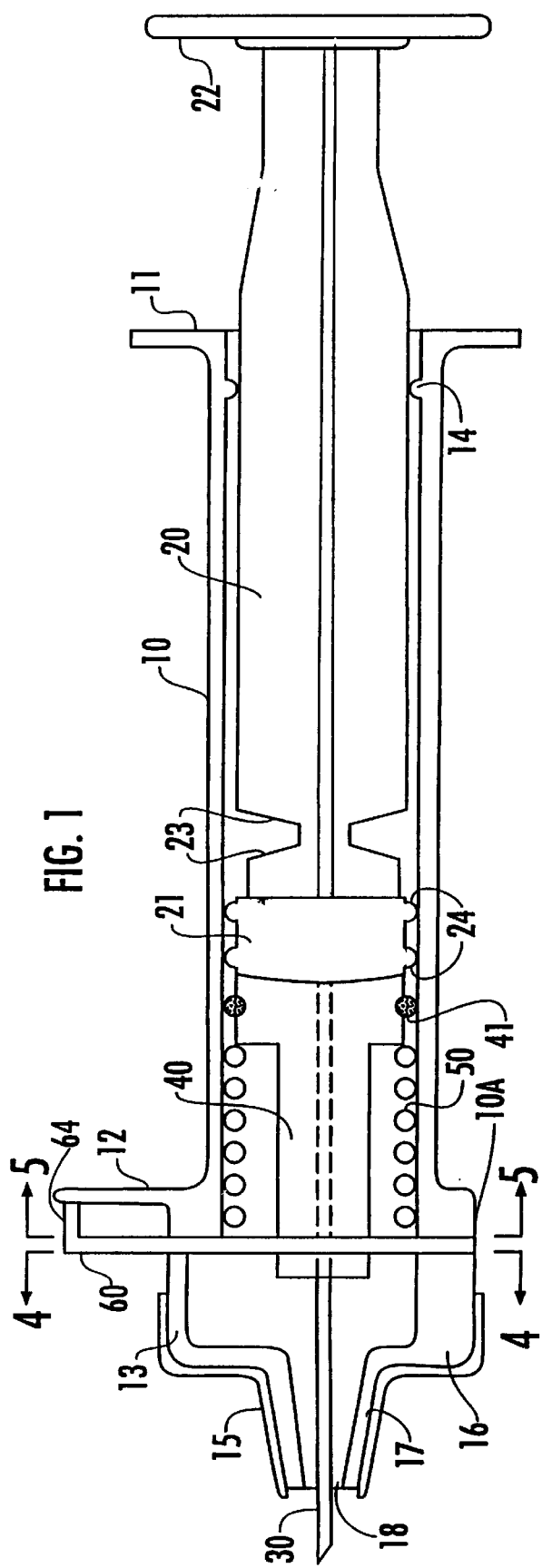
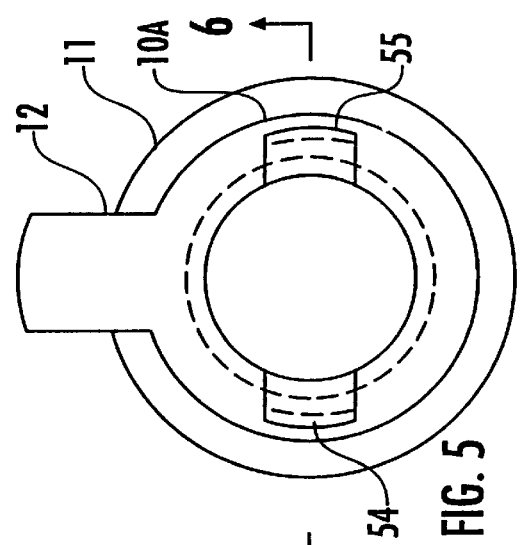
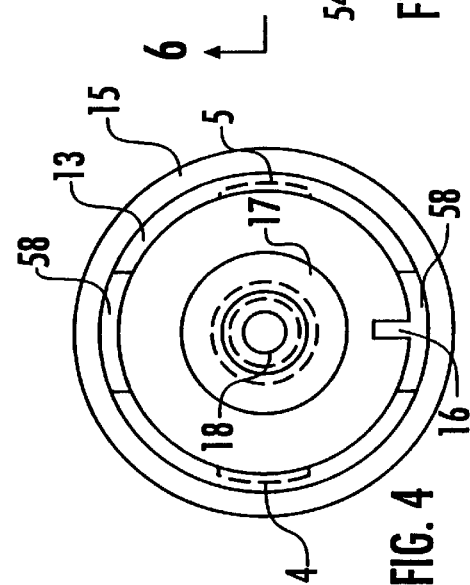
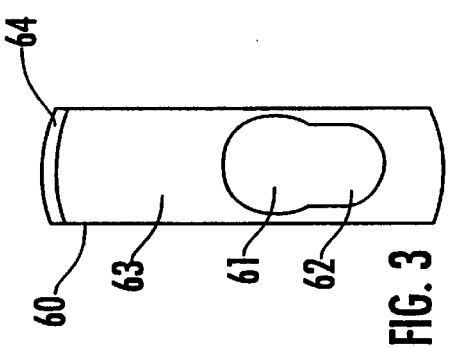

SPRING LOADED AUTOMATIC RETRACTABLE NEEDLE SYRINGE

BACKGROUND OF THE INVENTION

1. Field of the Invention

The present invention relates to a retractable needle safety syringe in which the needle may be withdrawn into the barrel of the syringe after use. More particularly the invention relates to a retractable needle syringe wherein the plunger need not be connected to the needle or its carrier for the retraction. Most particularly the invention relates to a retractable needle syringe wherein the needle carrier is spring loaded so that it may be automatically retracted into the syringe barrel after use.

2. Related Art

Due to the recent advent of the AIDS virus, which may be contracted by contaminated hypodermic syringes, there have been several retractable needle hypodermic syringes invented and patented. The retraction of the needle into the barrel of the syringe after use reduces the risk of "needle prick", or the accidental pricking of the person giving the injection after the syringe has been used.

Some of the recently patented retractable needle syringes include U.S. Pat. Nos. 4,692,156 (Haller); 4,675,005 (DeLuccia); 4,747,830 (Gloyer, et al); 4,790,822 and 4,950,251. All of the syringes disclosed include a hypodermic needle mounted on a carrier which is slidable in the barrel. The plunger is locked to this carrier after the injection has been given and is withdrawn up into the barrel by withdrawal of the plunger. The simplest mechanism for locking the plunger to the carrier is disclosed as a projection on the lower end of the plunger which engages through an opening in the upper end of the carrier.

One disadvantage of the above syringes is that the locking mechanism takes up some space in the barrel of the syringe and may prevent all of the measured liquid from being ejected by the plunger. This problem is exacerbated in the very small syringes such as the 1 cc tuberculin type. The liquid left in the barrel may be a substantial portion of the measured dose. In addition the narrowness of the barrel of the 1 cc syringe makes it difficult to design a needle carrier and locking that will fit in the barrel without enlarging the diameter so much as to make the calibration useless.

Venturini in U.S. Pat. No. 5,112,316 discloses a syringe similar to the retractable needle syringes described above except Venturini adds a spring outside the upper end of the syringe between the finger flange on the top of the barrel and the bottom surface of a projection at the top of the plunger to retract the plunger into the barrel after it has been locked onto the needle carrier. Venturini suffers the same draw backs because the plunger must still be locked to the needle carrier.

SUMMARY OF THE INVENTION

The present invention comprises a hollow barrel open at both ends and having plunger inserted through the distal end. At the proximal end is the needle or cannula (the terms are used interchangeably herein) firmly secured to a needle carrier. A compressed spring is placed between the needle carrier and the distal end of the barrel and a cap placed over the distal end. A releasable retaining means is provided to hold the needle carrier at the distal end. The needle extends through an opening in the end of the cap which is covered by a puncture pad. When the releasable retaining means is released the compressed spring pushes the needle carrier (and plunger if left in the barrel after use) back up completely into the barrel. The puncture pad seals the opening in the cap.

BRIEF DESCRIPTION OF THE DRAWING

FIG. 1 is a side view in partial cross section showing the internals of the syringe with the needle carrier locked in the forward position.

FIG. 3 is a front view of the releasable retaining means which hold the needle carrier in the forward position.

FIG. 4 is a view taken along line 4—4 of FIG. 1 showing the cap only.

FIG. 5 is a view taken along line 5—5 of FIG. 1 showing the barrel only.

DETAILED DESCRIPTION OF THE PREFERRED EMBODIMENT

Figure 2:
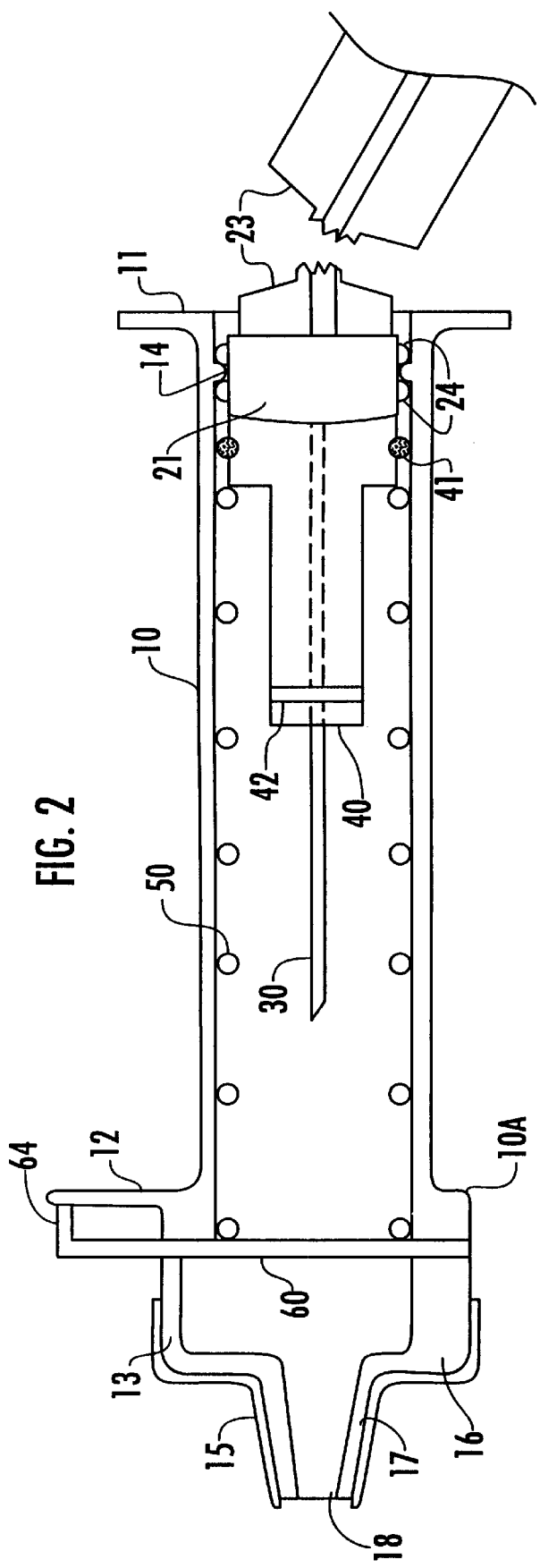
FIG. 2 is a side view in partial cross section showing the internals of the syringe with the needle carrier released and the plunger and needle carrier in the retracted position.

For a detailed description of the preferred embodiment the reader is directed to the accompanying figures in which like components are given like numerals for ease of reference.

Referring first to FIG. 1 there is shown an embodiment of the present invention in partial cross section. The syringe is seen to comprise a barrel 10 having a finger flange 11 at the distal end. A plunger 20 is inserted into the open distal end of the barrel 10. Surrounding the proximal end of the plunger 20 is a rubber piston 21 which sealably engages the inner wall of the barrel 10. The piston 21 is seen to have external circumferential edges 24 which upon retraction engage the internal circumferential ridge 14 near the distal end of the barrel 10. Also near the proximal end of the plunger is a notch 23 which makes the plunger frangible at this point and allows the plunger to be broken off after use.

At the proximal end of the barrel is an enlarged portion 10A which provides for the attachment of the cap 13 and surrounds the releasable retaining means 60. A radially extending tab 12 is provided to protect the releasable means 60 and prevent inadvertent release. In the proximal end of the barrel is located needle carrier 40 surrounded by compressed spring 50 which biases the needle carrier inward of the barrel and toward the distal end. Extending through the needle carrier is hypodermic needle 30. The needle 30 extends through the needle carrier 40. At the distal end of the needle carrier 40 is a circumferential o ring which sealably engages the inner wall of the barrel 10 and prevents liquid from passing into the portion of the barrel which contains the spring. The end of the needle carrier 40 is passed through the releasable retaining means 60 with the needle extending through an opening 18 in the cap 13. A rubber puncture pad 15 covers the opening through which the needle is passed. The proximal end of the needle carrier 40 is shaped to conform to the end of the piston 21.

Referring now to FIG. 3 the releasable retaining means is seen to comprise a small plate 63 having an opening 61 near the top which is slightly larger in diameter than the needle carrier. In addition the plate 63 has a slot 62 extending downward from the opening 60 which is slightly smaller in diameter than the needle carrier and which engages a circumferential groove 42 (seen in FIG. 2) near the proximal of the needle carrier 40 to hold the needle carrier at the proximal end as shown in FIG. 1. At the top of the plate is a tab 64 which extends distally along the syringe when place in the proximal end of the syringe.

Figure 6:
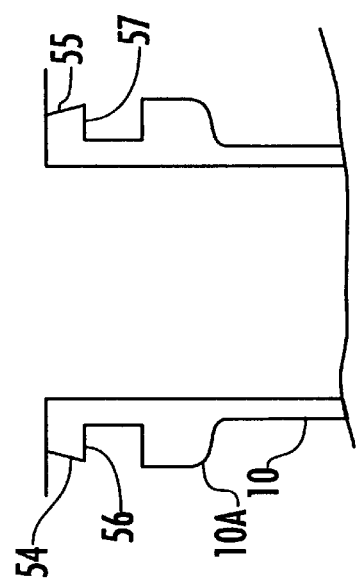
FIG. 6 is a view taken along line 6—6 of FIG. 5 showing the end of the barrel only.

Referring now to FIGS. 4–6 the details of the attachment of the cap 13 to the barrel 10 are shown. A pair of opposed semi-flexible projections 54 and 55 extend from the proximal end of the barrel 10. The projections each are tapered and have a flat surface 56 and 57 on the underside of the tapers. The cap 13 is pressed down over the projections which forces the tapers inward until the tapered ends engage internal notches 4 and 5 inside the cap 13. A slot 58 is provided in the cap 13 through which the releasable retaining means 60 slides. The guide 16 in the lower end of the cap 13 prevents the spring from forcing the lower end of the releasable retaining means 60 into the cap 13. Another simple method which is not shown is to provide external threads on the barrel and internal threads on the cap for attachment.

To retract the needle into the barrel after use the user presses radially inward on the tab 64 of the releasable retaining means 60 which slides the plate 63 downward until the opening 61 is aligned with the needle carrier 40. Since the opening 61 is slightly larger in the diameter than the needle carrier the carrier is released and the compressed spring pushes the needle carrier 40 distally back up into the barrel until the needle 30 is completely within the barrel as shown in FIG. 2. The groove 24 in piston 21 engages the ridge 14 on the inner wall of the barrel to secure the plunger at the distal end of the barrel 10. At this point the plunger can be broken to prevent further use. The needle 30 has been retracted through the puncture pad 15 which self closes and seals the proximal end of the syringe. The combination of the puncture pad 15 and the piston 21 provides seals at both ends of the barrel and makes a neat package for disposal. If desired, the plunger can be retracted and broken off before the needle carrier is released.

The invention claimed is:

1. A spring loaded automatic retractable needle syringe comprising:
   (a) a hollow barrel open at both ends having a finger flange about the distal end;
   (b) a plunger disposed through the open distal end of said barrel;
   (c) a needle carrier mounted in the proximal end and surrounded by a compressed spring which biases the needle carrier inward of said barrel and toward the distal end of said barrel, said needle carrier having an o-ring about the distal end to sealably engage the inner walls of said barrel;
   (d) a releasable retaining means mounted about said needle carrier to retain said needle carrier at the proximal end of said barrel and when released allows said spring to push said needle carrier inward of said barrel and toward the distal end of said barrel;
   (e) a cap having and opening at its proximal end mounted over the end of said barrel;
   (f) a self closing rubber puncture pad over said opening in said cap; and
   (g) a hypodermic needle secured to said carrier and extending through said puncture pad and said opening in said cap.

2. The spring loaded automatic retractable needle syringe according to claim 1 further comprising means to prevent inadvertent release of said releasable retaining means.

3. The spring loaded automatic retractable needle syringe according to claim 1 wherein said needle carrier has a circumferential groove near its proximal end and said releasable retaining means comprises (i) a plate slidably mounted between said cap and said barrel,
(ii) a slot in said plate which engages said circumferential groove, and
(iii) an opening above said slot which is slightly larger in diameter than said needle carrier.

4. The spring loaded automatic retractable needle syringe according to claim 1 further comprising an o-ring about said needle carrier to sealably engage said barrel.

5. The spring loaded automatic retractable needle syringe according to claim 1 further comprising a rubber piston disposed about the proximal end of said plunger.

6. The spring loaded automatic retractable needle syringe according to claim 5 further comprising a radially extending ridge on the inside of said barrel near the distal end of said barrel.

7. The spring loaded automatic retractable needle syringe according to claim 6 further comprising a circumferential groove about said rubber piston said circumferential groove engageable with said ridge.

8. A spring loaded automatic retractable needle syringe comprising:
   (a) a hollow barrel open at both ends having a finger flange about the distal end;
   (b) a plunger disposes through the open distal end of said barrel;
   (c) a needle carrier mounted in the proximal end and surrounded by a compressed spring which biases the needle carrier inward of said barrel and toward the distal end of said barrel, said needle carrier having an o-ring about the distal end to sealably engage the inner walls of said barrel;
   (d) a releasable retaining means mounted about said needle carrier to retain said needle carrier at the proximal end of said barrel and when released allows said spring to push said needle carrier inward of said barrel and toward the distal end of said barrel;
   (e) a cap having and opening at its proximal end mounted over the end of said barrel;
   (f) a hypodermic needle secured to said carrier and extending through said opening in said cap;
   (g) a self closing rubber puncture pad over said opening in said cap, said hypodermic needle extending through said puncture pad;
   (h) a rubber piston disposed about the proximal end of said plunger;
   (i) a radially extending ridge on the inside of said barrel near the distal end of said barrel; and
   (j) a circumferential groove about said rubber piston said circumferential groove engageable with said ridge.

9. A spring loaded automatic retractable needle syringe comprising:
   (a) a hollow barrel open at both ends having a finger flange about the distal end;
   (b) a plunger disposes through the open distal end of said barrel;
   (c) a needle carrier mounted in the proximal end and surrounded by a compressed spring which biases the needle carrier inward of said barrel and toward the distal end of said barrel, said needle carrier having circumferential groove near its proximal end and a circumferential o-ring about its distal end to sealably engage the walls of said barrel;
   (d) a releasable retaining means mounted about said needle carrier to retain said needle carrier at the proximal end of said barrel and when released allows said spring to push said needle carrier inward of said barrel and toward the distal end of said barrel, said releasable retaining means comprising;
(i) a plate slidably mounted between said cap and said barrel,
(ii) a slot in said plate which engages said circumferential groove, and
(iii) an opening above said slot which is slightly larger in diameter than said needle carrier;

(e) a cap having and opening at its proximal end mounted over the end of said barrel;
(f) a hypodermic needle secured to said carrier and extending through said opening in said cap; and
(g) a self closing rubber puncture pad over said opening in said cap, said hypodermic needle extending through said puncture pad.

* * * * *